United States Patent
Cho et al.

(10) Patent No.: US 10,005,969 B2
(45) Date of Patent: Jun. 26, 2018

(54) METHOD OF REMOVING CALCIUM FROM HYDROCARBON FRACTION USING EXTRACTION AGENT INCLUDING 2-OXOPROPANOL OR DERIVATIVES THEREOF

(71) Applicant: KOREA INSTITUTE OF ENERGY RESEARCH, Daejeon (KR)

(72) Inventors: Dong-Woo Cho, Daejeon (KR); Jong-Nam Kim, Daejeon (KR); Su Jin Jeong, Daejeon (KR); Hee Tae Beum, Daejeon (KR); Taesung Jung, Daejeon (KR); Hyung Chul Yoon, Daejeon (KR); Kanghee Cho, Daejeon (KR); Sang-Sup Han, Daejeon (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 0 days. days.

(21) Appl. No.: 15/606,181

(22) Filed: May 26, 2017

(65) Prior Publication Data
US 2017/0342329 A1 Nov. 30, 2017

(30) Foreign Application Priority Data
May 26, 2016 (KR) .................. 10-2016-0065116

(51) Int. Cl.
| | | |
|---|---|---|
| *C10G 29/22* | (2006.01) | |
| *C07C 49/185* | (2006.01) | |
| *C07B 63/00* | (2006.01) | |
| *B04B 5/00* | (2006.01) | |
| *C07F 3/04* | (2006.01) | |
| *G01N 21/75* | (2006.01) | |

(52) U.S. Cl.
CPC ............... *C10G 29/22* (2013.01); *B04B 5/00* (2013.01); *C07B 63/00* (2013.01); *C07C 49/185* (2013.01); *C07F 3/04* (2013.01); *G01N 21/75* (2013.01)

(58) Field of Classification Search
CPC .. C10G 29/22; C07F 3/04; B04B 5/00; C07C 49/185; C07B 63/00; G01N 21/75
See application file for complete search history.

(56) References Cited

U.S. PATENT DOCUMENTS

| | | | | |
|---|---|---|---|---|
| 3,876,135 A | * | 4/1975 | Harvey | .............. B01D 17/0217 494/37 |
| 5,593,573 A | | 1/1997 | Kramer | |

(Continued)

FOREIGN PATENT DOCUMENTS

| | | |
|---|---|---|
| JP | 2686309 A | 12/1989 |
| KR | 1020070078037 A | 7/2007 |

(Continued)

*Primary Examiner* — Randy Boyer
*Assistant Examiner* — Juan C Valencia
(74) *Attorney, Agent, or Firm* — STIP Law Group, LLC

(57) ABSTRACT

Disclosed is a method of removing calcium from a hydrocarbon fraction using an extraction agent including 2-oxopropanal or derivatives thereof, the method including (S1) adding a hydrocarbon fraction with an extraction agent including 2-oxopropanal or derivatives thereof to give a mixture, (S2) converting an oil-soluble calcium compound into a water-soluble calcium compound by reacting the hydrocarbon fraction with the 2-oxopropanal or derivatives thereof, and (S3) removing the water-soluble calcium compound.

7 Claims, 1 Drawing Sheet

(56) References Cited

U.S. PATENT DOCUMENTS

| | | |
|---|---|---|
| 6,905,593 B2 | 6/2005 | Kuehne et al. |
| 2014/0183102 A1* | 7/2014 | Subramaniyam ..... C07C 47/127 208/291 |
| 2015/0144457 A1* | 5/2015 | Ghosh ................... C10G 31/08 196/46 |

FOREIGN PATENT DOCUMENTS

| | | |
|---|---|---|
| KR | 101340718 A | 1/2008 |
| KR | 1020130087395 A | 8/2013 |
| KR | 101533599 B1 | 7/2015 |
| WO | WO2013024489 A1 | 2/2013 |

* cited by examiner

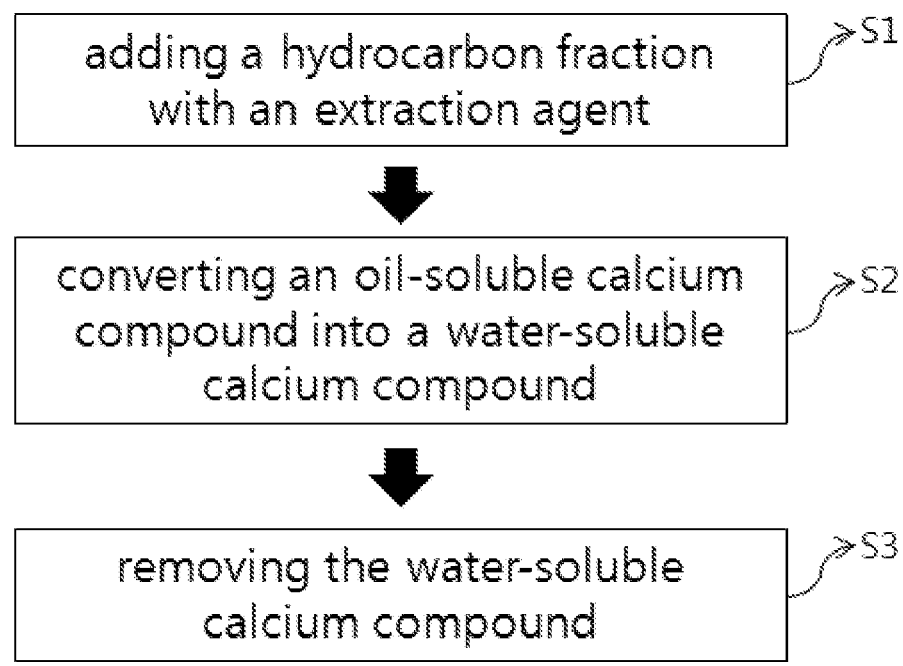

METHOD OF REMOVING CALCIUM FROM HYDROCARBON FRACTION USING EXTRACTION AGENT INCLUDING 2-OXOPROPANOL OR DERIVATIVES THEREOF

CROSS-REFERENCE TO RELATED APPLICATIONS

THE PRESENT APPLICATION CLAIMS THE BENEFIT OF KOREAN PATENT APPLICATION NO. 10-2016-0065116 FILED IN THE KOREAN INTELLECTUAL PROPERTY OFFICE ON May 26, 2016, THE ENTIRE CONTENTS OF WHICH ARE INCORPORATED HEREIN BY REFERENCE.

BACKGROUND OF THE DISCLOSURE

1. Technical Field

The present invention relates to a method of removing calcium from a hydrocarbon fraction, and more particularly to a method of removing calcium from a hydrocarbon fraction using an extraction agent including 2-oxopropanal or derivatives thereof.

2. Description of the Related Art

Generally, most onshore and offshore oil fields include heavy oil containing metal impurities such as calcium. In particular, among offshore oil fields containing large amounts of organic acids, during the production process, the organic acid contained in oil is coupled with a salt, especially calcium, contained in water supplied for oil production, thereby generating organic calcium. In some cases, such calcium is melted in oil, resulting in high calcium content in oil.

Such high-calcium oil has been excluded from development because of low economic benefits in the past, but the fact that high economic margin or sale margin are being ensured by virtue of processing of impurities is known these days, and many countries and companies have become interested in the development of related oil fields, and are actually involved in such development. Typical high-calcium oil fields include Doba and Kuito in West Africa and Heidrum and Captain in the North Sea, as well as Bohai Bay and Shengli in China and Serang in Indonesia, Asia. As shown by these examples, these high-calcium oil fields are distributed all over the world.

With regard to typical crude oil, calcium is mainly present in the form of a salt such as $CaCl_2$, and is easily removed through a desalting process. However, in the case of oil from oil fields, calcium is mostly present in the form of calcium naphthenate in which calcium is coupled with an organic acid such as naphthenic acid. Calcium naphthenate (CaNA) is configured such that the anion of naphthenic acid is coupled with the calcium cation, and also is characterized in that the chemical structure of the anion of naphthenic acid varies widely. Such calcium naphthenate, which is both hydrophilic and hydrophobic, is almost impossible to treat because it improves the stability of an emulsion produced during the desalting process.

Meanwhile, calcium in crude oil entails the following problems in the individual steps of the refinery process.

1) Oil tank farm—high BS&W (Basic sediment and water)

2) Desalting—emulsion level control, a decrease in voltage due to high conductivity of calcium (Ca)

3) Wastewater treatment—water carryover, poor effluent water quality

4) Heat exchanger and preheater—calcium deposits and low heat exchange efficiency 5) FCCU (Fluid Catalytic Cracking Unit) or RFCCU (Residue Fluid Catalytic Cracking Unit)—catalyst inactivation 6) High calcium content in coke and heavy fuel oil Because of these problems, high-calcium crude oil having high calcium content trades at lower prices than typical light oil. In the refinery industry, such high-calcium crude oil is being processed in a manner in which it is partially diluted with high-quality light oil.

These days, research is ongoing into methods of removing calcium from crude oil by removing calcium from calcium naphthenate using an acid compound such as sulfuric acid, carboxylic acid ester, water-soluble hydroxyl acid, or maleic acid.

U.S. Pat. No. 5,593,573 discloses the use of sulfuric acid or salts thereof as a calcium removal agent. In this case, an excess of precipitation inhibitor has to be used in order to prevent large amounts of calcium sulfate from being produced during the desalting process, which is undesirable.

Also, Korean Patent No. 10-1340718 discloses a method of removing calcium from a hydrocarbon fraction using maleic acid or derivatives thereof. When this method is applied to crude oil or hydrocarbon fractions containing water, precipitated calcium is known to flow up along the crude oil or hydrocarbon fraction, which is undesirable.

Therefore, it is necessary to develop a method of effectively removing calcium from a hydrocarbon fraction such as crude oil.

SUMMARY OF THE DISCLOSURE

Accordingly, the present disclosure has been made keeping in mind the problems encountered in the related art, and the present invention is intended to provide a method of effectively removing calcium from a hydrocarbon fraction using an extraction agent including 2-oxopropanal or derivatives thereof.

The above and other purposes and advantages of the present invention will become apparent from the following description of preferred embodiments.

Therefore, the present invention provides a method of removing calcium from a hydrocarbon fraction, comprising: (S1) adding a hydrocarbon fraction with an extraction agent including 2-oxopropanal or a derivative thereof to give a mixture; (S2) converting an oil-soluble calcium compound into a water-soluble calcium compound by reacting the hydrocarbon fraction with the 2-oxopropanal or derivative thereof; and (S3) removing the water-soluble calcium compound.

In (S1), the extraction agent may be added in an amount 0.1 to 100 times (based on a molar ratio) the amount of calcium contained in the hydrocarbon fraction, and the extraction agent may be added as a solid or as a mixed solution dissolved in water or an organic solvent. Here, when the extraction agent is added as the solid, stirring may be performed at 0 to 350° C. so as to form a homogeneous mixture, and when the extraction agent is added as the mixed solution dissolved in the water or organic solvent, stirring may be performed at 0 to 350° C. so as to form a homogeneous mixture.

(S2) may be performed at 0 to 350° C.

In (S3), the water-soluble calcium compound may be removed using gravity simply by being made to stand still based on a density difference, the water-soluble calcium compound may be removed through a centrifugation process using centrifugal force, or the water-soluble calcium compound may be removed through an electric desalting process using an electric field or through electric coalescence.

Also, the hydrocarbon fraction may be at least one selected from the group consisting of crude oil, bio oil, bio diesel, tight oil, shale oil, oil sand, liquefied coal oil, tar sand, atmospheric residue (AR), vacuum residue (VR), and a hydrocarbon residue.

According to the present invention, a calcium component (in organic metal form) can be efficiently removed from a hydrocarbon fraction containing a large amount of calcium.

Specifically, an increase in the quality of the hydrocarbon fraction containing a large amount of calcium can be achieved, conventional problems (use of excess precipitation inhibitor) can be overcome, and high calcium removal efficiency is assured to thus generate economic benefits and improve energy efficiency.

Furthermore, the present invention can be variously applied to a variety of facilities such as refinery facilities including desalting and dehydrating processes or hydrocarbon fraction-related onshore and offshore facilities.

The effects of the present invention are not limited to the foregoing, and other effects that are not mentioned herein will be more clearly understood to those skilled in the art through the following description.

BRIEF DESCRIPTION OF THE DRAWING

FIG. 1 schematically shows a process of removing calcium from a hydrocarbon fraction according to an embodiment of the present invention.

DETAILED DESCRIPTION OF THE DISCLOSURE

Hereinafter, a detailed description will be given of the present invention with reference to embodiments and drawing. These embodiments are merely set forth to illustrate, but are not to be construed as limiting the scope of the present invention, as will be apparent to those skilled in the art.

Unless otherwise defined, all technical and scientific terminologies used in the description of the present invention have the same meanings as those typically understood by those skilled in the art to which the present invention belongs. If there is a difference therewith, the description of the present specification, including definitions, will prevail.

In order to clearly illustrate the invention depicted in the drawing, parts not relevant to the explanation are omitted, and similar numbers refer to similar parts throughout the specification. As used herein, when any part "includes" any element, this means that another element is not excluded, but may be further included unless otherwise specifically mentioned. Also, the term "part" refers to a single unit or block that is responsible for a specific function.

The reference numerals (1, 2, etc.) in individual steps are used for the sake of description, and do not explain the order of the steps. Such steps may be executed differently from the described order unless the specific order is explicitly stated in context. That is, individual steps may be performed in the described order or in the reverse order, or may be substantially simultaneously conducted.

FIG. 1 schematically shows a process of removing calcium from a hydrocarbon fraction according to an embodiment of the present invention. With reference to FIG. 1, the method of removing calcium from the hydrocarbon fraction according to the embodiment of the present invention includes (S1) adding a hydrocarbon fraction with an extraction agent including 2-oxopropanal or derivatives thereof to give a mixture, (S2) converting an oil-soluble calcium compound into a water-soluble calcium compound by reacting the hydrocarbon fraction with 2-oxopropanal or derivatives thereof, and (S3) removing the water-soluble calcium compound. Here, the 2-oxopropanal derivative may include, but is not limited to, at least one selected from among pyruvic acid (CAS No.: 127-17-3), acetoacetic acid (CAS No. 541-50-4), propionaldehyde (Propanal, CAS No. 123-38-6), propanedial (CAS No.: 542-78-9), acetone (CAS No.: 67-64-1), diacetyl (CAS No.: 431-03-8), and acetylacetone (CAS No.: 123-54-6).

In the present invention, the extraction agent may include only 2-oxopropanal or derivatives thereof, but may be used in combination with a variety of conventional calcium extraction agents, as necessary. Examples of the conventional calcium extraction agent may include citric acid, hydrochloric acid (HCl), oxalic acid, ammonium hydroxide ($NH_4OH$), acetic acid, sulfuric acid, maleic anhydride, fumaric acid, maleic acid, tartaric acid, succinic acid, glycolic acid, and gluconic acid. When a natural separation process using gravity is performed to remove the water-soluble calcium compound in (S3), the use of an acid-based extraction agent is not preferable. This is because the acid-based extraction agent improves emulsion stability and thus water separation becomes somewhat difficult, adversely affecting the removal of calcium.

In the present invention, when the extraction agent including 2-oxopropanal or derivatives thereof is used, calcium may be efficiently removed from the hydrocarbon fraction. Specifically, the extraction agent including 2-oxopropanal or derivatives thereof exhibits high stability compared to conventional acid-based extraction agents (sulfuric acid, maleic acid, etc.) or glyoxal, and the efficiency of removal of calcium from the hydrocarbon fraction is high, as will be described in the following Examples.

2-oxopropanal is produced as the byproduct of several metabolic pathways from organisms. Specifically, it may be produced from 3-aminoacetone, which is an intermediate of lipid peroxidation and threonine catabolism, and is mainly produced by glycolysis. It is produced from two intermediates of glycolysis, for example, glyceraldehyde phosphate and dihydroxyacetone phosphate, through nonenzymatic phosphate elimination. It has different synthesis routes (using different starting materials) from glyoxal resulting from gas-phase oxidation of ethylene glycol in the presence of a silver or copper catalyst or liquid-phase oxidation of acetaldehyde in the presence of nitric acid. Also, glyoxal reacts with an oil fraction due to its high reactivity and is toxic, whereas 2-oxopropanal is less harmful than glyoxal.

Here, the hydrocarbon fraction is an oil, which is composed mainly of carbon and hydrogen and is not mixed with water. Examples of the hydrocarbon fraction may include crude oil, bio oil, bio diesel, tight oil, unconventional oil, shale oil, oil sand, liquefied coal oil, tar sand, atmospheric residue (AR) resulting from or collected downstream of a crude oil refinery, vacuum residue (VR), hydrocarbon residue, and refinery and petrochemical byproducts.

In an embodiment of the present invention, (S1) is a step of preparing a mixture by adding a hydrocarbon fraction with an extraction agent including 2-oxopropanal or derivatives thereof. Here, the extraction agent including 2-oxopropanal or derivatives thereof is preferably added in an amount 0.1 to 100 times, and more preferably 0.1 to 10 times (based on a molar ratio), the amount of calcium contained in the hydrocarbon fraction. If the amount of the 2-oxopropanal or derivatives thereof is less than 0.1 times the amount of calcium, the amount of remaining calcium is too low, and thus the effect of removing calcium is insignificant. On the other hand, if the amount thereof exceeds 100 times, the removal efficiency is not further improved, thus negating economic benefits.

Also, the extraction agent including 2-oxopropanal or derivatives thereof may be added in the form of a solid to the hydrocarbon fraction, or may be added in the form of a mixed solution dissolved in water or an organic solvent. The present invention may be separately applied to an oil production process for producing a high-calcium hydrocarbon fraction (i.e. an onshore or offshore facility for producing high-calcium crude oil) and a refinery process for processing a high-calcium hydrocarbon fraction. In the case of the oil production process, the amount of water in the oil from the oil well may fall in the range from 1 wt % to 99 wt %. In the case of the refinery process, 0.5 wt % water is contained in crude oil from an oil tank farm. Accordingly, even when the extraction agent including 2-oxopropanal or derivatives thereof is directly added as a solid, it may be dissolved by water contained in oil alone. Alternatively, in order to control the concentration of 2-oxopropanal or derivatives thereof in the extraction agent, it may be first dissolved in water, an organic solvent or a demulsifier and may then be mixed with crude oil or a hydrocarbon fraction.

When the extraction agent including 2-oxopropanal or derivatives thereof is directly added as a solid to the hydrocarbon fraction, it is preferred that a homogeneous mixture be prepared. In order to provide such a homogeneous mixture, any known process may be performed, and stirring may be performed in the temperature range of 0 to 350° C., and preferably 10 to 250° C. The stirring time ranges from ones of sec to ones of hr, and preferably from 10 sec to 1 hr. As mentioned above, the extraction agent may be dissolved by water present in the hydrocarbon fraction. In the case of a hydrocarbon fraction having no water or relatively low water content, water, an organic solvent or a demulsifier may be further added. Here, the extraction agent may be used by being appropriately diluted in a concentration range of 1 to 99%. In this case, uniform mixing is also regarded as important.

Also, when the extraction agent including 2-oxopropanal or derivatives thereof is added in the form of a mixed solution dissolved in water, an organic solvent or a demulsifier, it is important that the extraction agent be uniformly mixed with the water, organic solvent or demulsifier. The uniform mixing may be performed using any known mixing process, and stirring is carried out in the temperature range from 0 to 350° C., preferably 10 to 250° C., and more preferably 10 to 170° C. Also, the stirring time falls in the range of 10 sec to one day, and preferably 10 sec to 1 hr. Stirring is performed so that the extraction agent that is added is completely dispersed and sufficiently dissolved, thus obtaining a mixed solution in a homogeneous phase. Here, examples of the organic solvent may include alcohols (monohydric or polyhydric alcohols), acetones, ketones, esters, glycols, and ethers/esters.

In an embodiment, (S2) is a step of chemically reacting the hydrocarbon fraction with the extraction agent including 2-oxopropanal or derivatives thereof, and is specifically performed in a manner in which the hydrocarbon fraction and 2-oxopropanal or derivatives thereof are reacted so that an oil-soluble calcium compound such as calcium naphthenate is converted into a water-soluble calcium compound such as a calcium ion or calcium salt. Here, water or an organic solvent may be further added so as to effectively remove the water-soluble calcium ion or calcium salt in (S3).

Particularly in (S2), it is important that stirring be performed to achieve complete mixing in a reactor so as to carry out an efficient chemical reaction between the hydrocarbon fraction, having high viscosity, and the extraction agent. Moreover, in the case of a continuous process, a mixing pump or a centrifugal pump having high miscibility may be used, thus exhibiting high mixing efficiency compared to when a typical batch process is applied. Furthermore, in order to efficiently carry out such a chemical reaction in the reactor, the reaction is performed in the temperature range of 0 to 350° C., and the reaction time may fall in the range from ones of sec to ones of hr, and preferably 1 min to 1 hr.

In an embodiment, (S3) is a step of removing the water-soluble calcium compound such as a calcium ion or calcium salt formed in (S2). The water-soluble calcium compound may be removed in various manners, and may include a natural separation and removal process using gravity by being made to stand still based on a density difference, a centrifugation and removal process using centrifugal force, an electric desalting process using an electric field, or a separation and removal process using electric coalescence.

In the step of removing the water-soluble calcium compound, a demulsifier may be added to further increase the removal efficiency. The demulsifier may include polyol, polyamine, amine, etc., and the amount of the demulsifier may be about 1 to 10000 ppm, and preferably 10 to 100 ppm based on the total amount of the mixture (comprising the hydrocarbon fraction and the extraction agent). If the amount thereof is less than 1 ppm, the effect becomes insignificant due to the small amount thereof. On the other hand, if the amount thereof exceeds 10000 ppm, the extent of increasing the removal efficiency is insignificant, thus negating economic benefits.

The process of removing the water-soluble calcium compound using gravity (natural separation) is performed depending on the gravity and density difference using a difference in specific gravity between the aqueous solution phase and the oil phase. Here, a separator may be used. Specifically, this process may be implemented at 0.5 to 99 wt % of water based on the total amount of the mixture in the temperature range of 10 to 350° C. for a retention time ranging from ones of min to ones of hr.

The process of removing the water-soluble calcium compound using centrifugation (a centrifugation process) may be performed at a g-force of 10 to 1000 based on ASTM, and is specifically conducted at 100 to 15000 rpm, and preferably 500 to 10000 rpm for a period of time ranging from ones of min to 48 hr and preferably 10 min to 24 hr. Here, the temperature range may fall in the range of 10 to 350° C.

The process of removing the water-soluble calcium compound (an electric desalting process) through electric desalting or electric coalescence may be conducted using a typical electric desalting device under conditions of a direct current or alternating current of 100 to 10,000 V/cm, a time period of 5 min to 3 hr, and preferably 5 min to 1 hr, and a temperature of 10 to 350° C. Here, the amount of water that is used is 0.01 to 50 wt %, and preferably 0.01 to 20 wt % based on the total amount of the mixture. As an additional additive, a demulsifier may be used in an amount of 1 to 100 ppm, and preferably 2 to 50 ppm based on the total amount of the mixture.

A better understanding of the construction and effects of the present invention may be obtained through the following Examples and Comparative Examples, which are merely set forth to illustrate but are not to be construed as limiting the scope of the present invention.

TEST EXAMPLE

The removal of calcium from crude oil (high-calcium crude oil) containing calcium using 2-oxopropanal and other extraction agents was tested (centrifugation, natural separation, and electric desalting). The high-calcium crude oil contained 100 ppm of calcium. The calcium removal rate indicates a removal efficiency calculated from Equation 1 below by measuring the concentration ($C_{Ca,0}$) of a crude oil sample before the calcium removal test and the concentration ($C_{Ca}$) after the calcium removal test.

$$(C_{Ca,0}-C_{Ca})/C_{Ca,0} \times 100 \quad \text{(Equation 1)}$$

Example 1

Oil-water Separation Using Centrifugation

Each of various calcium extraction agents in an amount four times the molar amount of calcium contained in the high-calcium crude oil was dissolved in tertiary distilled water to give each extraction solution. 60 g of high-calcium crude oil and 20 g of the extraction solution were mixed using a blender and then stirred at 90° C. and 7200 rpm for 10 min. After the completion of the reaction, the calcium compound was removed at 3500 rpm for 24 hr using a centrifuge.

After the completion of centrifugation, layer separation between the oil layer of the high-calcium crude oil and the aqueous solution layer was allowed to occur. The oil layer, corresponding to the supernatant, was separated and subjected to ICP, whereby the remaining calcium concentration was analyzed. The results are shown in Table 1 below.

TABLE 1

| Calcium extraction agent | Calcium removal rate (%) |
|---|---|
| 2-oxopropanal | 91.18 |
| Glyoxal | 87.25 |
| trans-Aconitic acid | 39.22 |
| Pyruvic acid | 23.53 |
| Formic acid | 45.1 |
| Glyoxylic acid | 51.96 |

As is apparent from the results of Table 1, when 2-oxopropanal was used as the extraction agent of the calcium component, calcium could be removed at very high efficiency from the high-calcium crude oil, compared to when using the other extraction agents.

Example 2

Removal of Emulsion Using Gravity and Density Difference

High-calcium crude oil and water were mixed at a volume ratio of 70:30 at a middle intensity using a blender for 20 sec, thus obtaining an emulsion. Thereafter, each of various calcium extraction agents in an amount two times the molar amount of calcium contained in the high-calcium crude oil and 100 ppm of a demulsifier were added, and further mixed at a middle intensity for 20 sec using a blender. After the mixing, the resulting mixture was placed in a vial, closed with a cover, and then allowed to stand at 80° C. for 1 hr. After 1 hr, the upper layer was obtained and the calcium concentration thereof was measured using ICP-AES. The results are shown in Table 2 below.

TABLE 2

| Extraction agent | Calcium removal rate (%) |
|---|---|
| 2-oxopropanal | 94.11 |
| Glyoxal | 75.35 |
| trans-Aconitic acid | 34.51 |

As is apparent from the results of Table 2, when 2-oxopropanal was used as the extraction agent of the calcium component, calcium could be removed at very high efficiency from the high-calcium crude oil, compared to when using the other extraction agents.

Example 3

Separation Using Electric Desalting

High-calcium crude oil pre-warmed at 90° C., and washing water containing 2-oxopropanal in an amount two times the molar amount of calcium contained in the crude oil, were mixed at a volume ratio of 90:10, and 1000 ppm of a demulsifier was further added, followed by mixing for 10 min at a strong intensity using a blender, thus obtaining an emulsion. After the mixing, the resulting mixture was placed in a vial for exclusive use in a batch-type electric desalter, and an electric power of 8000 V was applied thereto at 87° C. for 30 min. Thereafter, the upper layer was obtained and the calcium concentration thereof was measured using ICP-AES. The calcium removal rate was 92%.

Although the preferred embodiments of the present disclosure have been disclosed for illustrative purposes, those skilled in the art will appreciate that various modifications, additions and substitutions are possible, without departing from the scope and spirit of the invention as disclosed in the accompanying claims.

What is claimed is:

1. A method of removing calcium from a hydrocarbon fraction, comprising:
   (S1) adding a hydrocarbon fraction with an extraction agent including 2-oxopropanal or a derivative thereof to give a mixture,
   wherein the extraction agent is added as a solid and stirring is performed at 0 to 350° C. so as to form a homogeneous mixture;
   (S2) converting an oil-soluble calcium compound into a water-soluble calcium compound by reacting the hydrocarbon fraction with the 2-oxopropanal or derivative thereof; and
   (S3) removing the water-soluble calcium compound.

2. The method of claim 1, wherein in (S1), the extraction agent is added in an amount 0.1 to 100 times (based on a molar ratio) an amount of calcium contained in the hydrocarbon fraction.

3. The method of claim 1, wherein (S2) is performed at 0 to 350° C.

4. The method of claim 1, wherein the removing the water-soluble calcium compound in (S3) is performed using gravity.

5. The method of claim 1, wherein the removing the water-soluble calcium compound in (S3) is performed using a centrifugal force.

6. The method of claim 1, wherein the removing the water-soluble calcium compound in (S3) is performed through electric desalting using an electric field or through electric coalescence.

7. The method of claim 1, wherein the hydrocarbon fraction is at least one selected from the group consisting of crude oil, bio oil, bio diesel, tight oil, shale oil, oil sand, liquefied coal oil, tar sand, atmospheric residue (AR), vacuum residue (VR), and a hydrocarbon residue.

* * * * *